United States Patent [19]

Toth

[11] Patent Number: 4,728,173

[45] Date of Patent: Mar. 1, 1988

[54] OPTICAL FILTER FOR PROTECTIVE WELDING LENS ASSEMBLIES

[76] Inventor: Peter Toth, Smålandsgatan 9, S-293 00 Olofström, Sweden

[21] Appl. No.: 704,189

[22] Filed: Feb. 22, 1985

[30] Foreign Application Priority Data

Feb. 24, 1984 [SE] Sweden ................................ 8401003

[51] Int. Cl.⁴ .......................... G02F 1/133; B23K 9/22
[52] U.S. Cl. .................................... 350/332; 219/147; 350/335; 350/339 F
[58] Field of Search ................... 350/335, 337, 339 F, 350/349, 281, 278, 279, 283, 332; 219/147; 2/8

[56] References Cited

U.S. PATENT DOCUMENTS

| | | |
|---|---|---|
| 3,575,491 | 4/1971 | Heilmeier . |
| 3,612,666 | 10/1971 | Rabinow .......................... 350/281 |
| 3,703,329 | 11/1972 | Castellano ....................... 350/349 |
| 3,781,465 | 12/1973 | Ernstoff et al. ................ 350/349 X |
| 3,967,881 | 7/1976 | Moriyama et al. . |
| 4,071,912 | 2/1978 | Budmiger ...................... 350/339 F |
| 4,154,746 | 3/1979 | Huffman ............................ 350/349 |
| 4,240,709 | 12/1980 | Hornell ............................. 350/335 |
| 4,241,339 | 12/1980 | Ushiyama ......................... 350/349 |
| 4,497,543 | 2/1985 | Aoki et al. ....................... 350/349 |
| 4,527,864 | 7/1985 | Dir .................................... 350/337 |
| 4,541,693 | 9/1985 | Knoll et al. ................... 350/339 F |

FOREIGN PATENT DOCUMENTS

| | | | |
|---|---|---|---|
| 0092276 | 7/1980 | Japan ............................... 219/147 |
| 0111102 | 6/1984 | Japan ............................... 350/278 |
| 394755 | 3/1974 | Sweden . | |

*Primary Examiner*—Stanley D. Miller
*Assistant Examiner*—David Lewis
*Attorney, Agent, or Firm*—Shapiro and Shapiro

[57] ABSTRACT

An optical filter for welding protective lens assemblies has two parallel electro-optical cells, at least one of the cells being of the nematic type with admixture of dye molecules with anisotropic light absorption. The filter comprises a filter sheet disposed in the ray path of the cells and allowing transmission within a wave range which is offset with respect to the wave range within which said one cell is transmitting residual light in its absorbing state.

6 Claims, 9 Drawing Figures

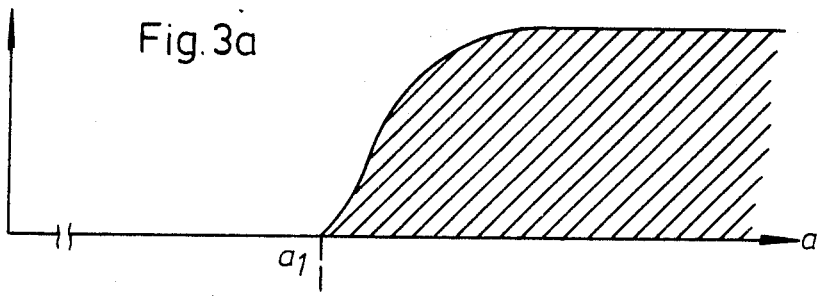
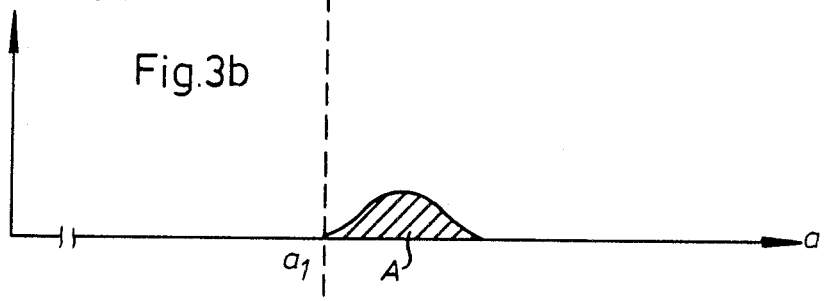
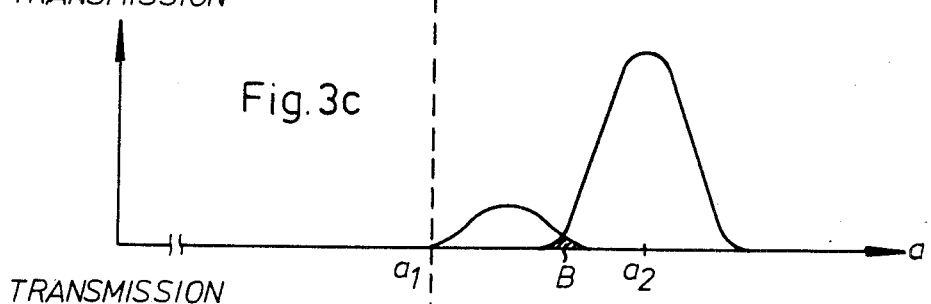
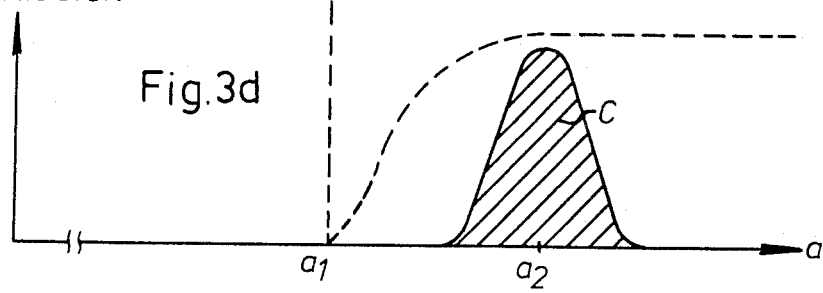

OPTICAL FILTER FOR PROTECTIVE WELDING LENS ASSEMBLIES

BACKGROUND OF THE INVENTION

1. Field of the Invention

The present invention generally relates to electro-optical cells (EO-cells) which comprise two transparent electrodes and a layer of liquid crystals interposed between said electrodes. The invention more specifically relates to an optical filter for use in a protective welding lens assembly in a welder's helmet or visor, said filter being made up of EO-cells of the above-mentioned type and having a filter sheet disposed in the ray path for eliminating residual light.

2. Description of the Prior Art

Electro-optical cells using liquid crystals have been suggested for and also come into practical use in protective welding lens assemblies. This has conferred the advantage that the visor of the welder's helmet need not be raised and lowered between the different welding operations.

The electro-optical filters hitherto suggested and used do however not meet all the demands which should be placed on e.g. a protective welding lens assembly.

SUMMARY

It is desirable, for instance, that such protective lens assemblies have a substantially angle-independent transmission and absorption capacity which is not found in hitherto known protective welding lens assemblies using liquid crystals of the nematic type. Further, the lens assembly should switch from the light-transmitting to the light-absorbing state so quickly that there is no risk of eye damage and, moreover, perform such switching in direct dependence upon the appearance of the welding light and independently of other ambient conditions. Finally, it is also necessary that the protective welding lens assembly does not become light-transmitting upon voltage drop-out.

An object of the present invention therefore is to provide an optical filter of the type mentioned by way of introduction, which complies with the desiderata stated above.

This and further objects of the invention are achieved in that the optical filter in protective welding lens assemblies, comprises two parallel electro-optical cells each of which has a light transmission which is dependent on the voltage applied across two transparent electrodes included in the respective cell and having intermediate layers of liquid crystals, one of said cells being light-transmitting when voltage is applied and light-absorbing when voltage is not applied, wherein at least a first of said cells is of the nematic type with an admixture of dye molecules with anisotropic light absorption, the filter further comprising a filter sheet disposed in the ray path of the cells and allowing transmission within a wave range which is offset with respect to the wave range within which the first cell is transmitting residual light in its absorbing condition.

As regards switching control of electro-optical filters in dependence upon the appearance of welding light, it should be mentioned that problems have previously been encountered in finding a suitable trigger point in relation to the ambient light. Attempts have also been made to use a light-sensing element of high spectral dependence, which has however met with little success.

The invention ensures adequate and rapid switching as well as automatic detection of the welding light without the need of any sensitivity-adjusting means and independently of the strength and nature of the ambient light. Contributory to the rapid switching is also the fact that a bias voltage has already been applied across the electrodes before switching occurs, this bias voltage being insufficient for making the cell light-absorbing but allowing a quicker switching of the cell when a voltage of sufficient magnitude, preferably of exaggerated magnitude of short duration, is applied to said cell. Such a method of applying a bias voltage prior to switching is disclosed in, for instance, SE No. 394,755, and a method of obtaining a shorter switching time by using a voltage of exaggerated magnitude of short duration is disclosed in U.S. Pat. No. 3,575,491.

The optical filter according to the invention yields considerably improved light angles as compared with the optical filters which are currently used in protective welding lens assemblies. Thus, this improvement is achieved in that at least one of the two electro-optical cells of the optical filter has an admixture of dye molecules with anisotropic light absorption. An optical display unit of such a design is disclosed in, for instance, U.S. Pat. No. 3,967,881. This means that along the long axes of the dye molecules plane-polarized light is absorbed more strongly than light polarized at right angles to the long axes of the dye molecules. An electro-optical cell of this type may thus be regarded as an electrically controlled colour filter which is switchable between one state in which it is light-transmitting or transparent, and another state in which it transmits light of substantially one wavelength, i.e. "coloured" light. The major advantage of an electro-optical cell of the type having an admixture of dye molecules with anisotropic light absorption is that the transmission and absorption properties of the cell are substantially completely independent of the viewing angle through the cell.

When electro-optical cells of the type described above are used in protective welding lens assemblies, there is however a problem as regard the incomplete light absorption of the cells during the welding operation. This applies in particular to the above-described "colour cell" in which the transmitted residual light in the absorbing state of the cell may cause damage to the human eye.

In order to solve this problem, a filter sheet is provided in the optical filter according to the invention for eliminating said residual light. This solution profits from the fact that the residual light is within a limited wave range.

In an optical filter according to the invention, the second electro-optical cell may be a cell similar to the first cell or an electro-optical cell of the type used in present-day protective welding lens assemblies, i.e. an electro-optical cell having a liquid crystal layer of the nematic type without admixture of dye molecules with anisotropic light absorption.

By combining the optical filter according to the invention with suitable polarizing filters and filter sheets, it can be made up in many different ways of "positive" and "negative" electro-optical cells. In this context, "positive" means that the cell is light-absorbing when a voltage is applied across its electrodes, and "negative" consequently means a cell which is light-transmitting when voltage is applied and, hence, light-absorbing when voltage is not applied. In this connection, it should also be pointed out that the electro-optical cells in the light-absorbing state and the associated filter sheet do not absorb the incident light completely and so, a welding operation can be viewed through such an optical filter when it is in its light-absorbing state.

In the following text, the designation TN-cell will be used for an electro-optical cell with liquid crystals of the twisted-nematic type, which cell, in addition to the crystal layer with associated electrodes, also comprises two polarizing filters. The designation GH-cell is an abbreviation for "Guest-Host" cell and relates to a liquid crystal of the nematic type doped with anisotropically light-absorbing dye molecules, and pertaining electrodes.

BRIEF DESCRIPTION OF THE DRAWINGS

The invention will be described in greater detail hereinbelow with reference to the accompanying drawings, in which

FIGS. 3a-d are transmission-wavelength graphs which describe the function of the filter sheet according to the invention;

DESCRIPTION OF THE PREFERRED EMBODIMENTS

Figures 1, 2:
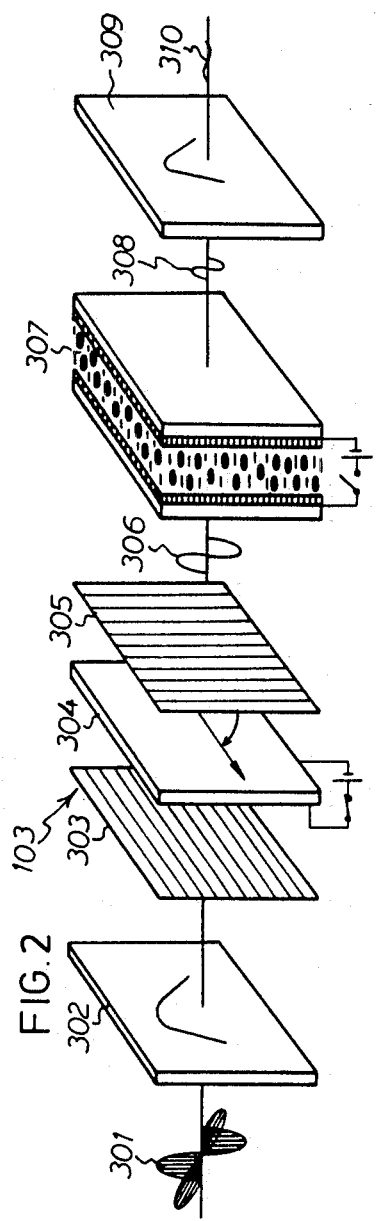
FIG. 1 is a perspective view of the interior of a welder's helmet or visor provided with the optical arrangement according to the present invention.
FIG. 2 schematically shows the design of a preferred embodiment of the optical arrangement according to the invention, i.e. the optical filter, in the welder's helmet or visor.

FIG. 1, to which reference is now made, illustrates a welder's visor 101 provided with a pressure-sensitive switch 102 which is arranged in such a manner that it switches states when the user puts on the visor, an optical unit 103 through which the user observes the welding operation and in which light attenuation increases substantially during the welding operation, and a head band 104 which serves to keep the visor 101 in place. The visor may also be hingedly mounted such that the user can raise the entire visor without having to take off the head band in order to have a better survey of his work.

FIG. 2 shows a preferred embodiment of the optical arrangement 103 which in the direction of incidence of the welding light comprises a UV-IR protective filter 302, a first electro-optical cell 303, 304, 305 of the TN-type, a second electro-optical cell 305, 307 of the GH-type, and a filter sheet 309 according to the invention.

A first reason for this design is that it is desirable to make use of the short switching time of the TN-cell from the non-energized to the energized state. Since it is the switching time from light to dark cell that is critical, a positive TN-cell 303, 304, 305 has been selected. A second reason is the unfavourable asymmetric light transmission properties as compared with the GH-cell, when the viewer is looking in different directions through the cell. A third reason is that it is desirable by means of the filter sheet 309 to eliminate residual light leaving the GH-cell in the absorbing state thereof. Since current safety regulations for such visors provide that a voltage drop-out should not entail that the user is exposed to welding light passing through the optical arrangement, a negative GH-cell 305, 307 has been selected.

The TN-cell 303, 304, 305 consists of (a) a layer 304 of liquid crystals whose molecules are in the so-called twisted-nematic phase, i.e. are located mutually parallel in rotated parallel layers, (b) two transparent electrodes which are located on the main plane of the crystal layer and which make it possible to apply an electric field across the crystal layer, (c) a first polarizing filter, hereinafter termed P-filter 303, which is disposed parallel to the crystal layer at the input side thereof, (d) a second P-filter 305 which has a direction of polarization at right angles to the direction of polarization of the first P-filter 303 and is located parallel to the crystal layer at the output side thereof.

By means of an external voltage source, it is possible to control the transmittance of the TN-cell in the following manner. If the crystal (crystal layer) is non-energized, the direction of polarization of the incident polarized light is rotated 90° in the crystal, which means that the light issuing from the crystal 304 can pass unimpededly through the second P-filter 305. If, on the other hand, the crystal 304 is energized by a suitable electric field, the layers of the crystal will be rotated in relation to each other in such a manner that the resulting light rotation in the crystal becomes zero. The light issuing from the crystal 304 thus is orthogonally polarized with respect to the second P-filter 305 and consequently blocked by this filter. An EO-cell of the type described above is a so-called positive cell, i.e. it transmits light in the non-energized state and strongly attenuates light in the energized state. The opposite applies to a so-called negative EO-cell.

The second electro-optical cell shown in FIG. 2 is of the so-called guest-host type or GH-type and consists of (a) a layer 307 of a nematic liquid crystal (host) doped with organic molecules (guest), (b) two transparent electrodes (not shown) which are disposed on the main plane of the crystal layer and which make it possible to apply an electric field across the crystal layer 307, (c) the P-filter 305 which is also included in the TN-cell and is located parallel to the crystal layer 307 at the input side thereof. FIG. 2 also shows the filter sheet 309 according to the invention which, in the present embodiment, is disposed parallel to the crystal layer 307 at the output side thereof.

As in the case of the TN-cell 303, 304, 305, it is also possible to control the transmittance of the GH-cell 305, 307 by applying an electric field of varying magnitude across the electrodes. The organic molecules dissolved in the crystal (crystal layer) 307 are absorbing light only if the direction of polarization thereof is oriented in a certain way in relation to a certain axis in the molecules. If the crystal is non-energized, these "dye molecules"

are randomly oriented in the crystal and absorb light on an average, the crystal in this non-energized state allowing light only within a certain wave range to pass, i.e. light having a certain colour.

However, if the crystal 307 is energized, the crystal molecules are oriented according to the electric field and the asymmetric dye molecules are forced to follow this order and are thus oriented such that no light is absorbed in the crystal. In the energized state, the GH-cell thus is transparent, i.e. the cell is of the negative type.

Before the welding operation is started, the TN-cell is substantially non-energized and the GH-cell is energized, which means that the attenuation or contrast is low in both cells. However, the incident light 301 is filtered in the protective filter 302 and is attenuated in the P-filter 303, the crystal 307 and the filter sheet 309 in FIG. 2. In order to improve the switching time of the TN-cell, it is suggested to apply a small bias voltage across the crystal 304 according to known technique. When the welding operation starts, the voltage is increased over the crystal 304 and decreased over the crystal 307, as shown in FIG. 2, which entails that the attenuation increases in both EO-cells. The light 306 which passes through the TN-cell is further attenuated in the crystal 307 and thereafter practically completely extinguished (area B in FIG. 3c) when passing through the colour filter 309, as illustrated by reference numerals 308 and 310, respectively.

In order further to clarify the advantage of the filter sheet 309 according to the invention, the function of the filter sheet in the optical filter will be described in greater detail hereinbelow with reference to graphs 3a–d.

Graph 3a shows the light transmission of the filter in the transmitting state thereof as a function of the wavelength when the filter sheet 309 according to the invention is not used, the wavelength $\lambda_1$ representing the upper wavelength boundary of the input filter 302.

In its absorbing state, and still without the filter sheet 309, as described in e.g. the above-mentioned U.S. Pat. No. 3,967,881, the optical filter during welding transmits a quantity of residual light corresponding to the hatched area A in graph 3b.

By providing in the ray path of the cells, as shown in FIG. 2, a filter sheet 309 of a colour other than that of the light which the GH-cell 305, 307 allows to pass in its absorbing state, i.e. the filter sheet 309 in accordance with the invention has its transmission within a wave range which is offset in relation to the wave range within which the GH-cell is transmitting residual light in its absorbing state, a small quantity of light corresponding to the hatched area B in graph 3c is transmitted during welding. This should be compared with area A in graph 3b and thus is a considerable improvement as regards the light-dark contrast as compared with prior techniques used in protective welding lens assemblies.

The location of the filter sheet 309 in the ray path in relation to the TN-cell and the GH-cell obviously is unessential, and the location of the filter sheet at the output side of the GH-cell in FIG. 2 should thus be regarded merely as an example.

Further, it should be pointed out that the hatched area C in graph 3d corresponds to the quantity of light emerging from the filter in its light-transmitting state when use is made of said filter sheet 309 according to the invention. The transmission range of the filter sheet therefore is within the sensitive range of the eye.

Figure 4:
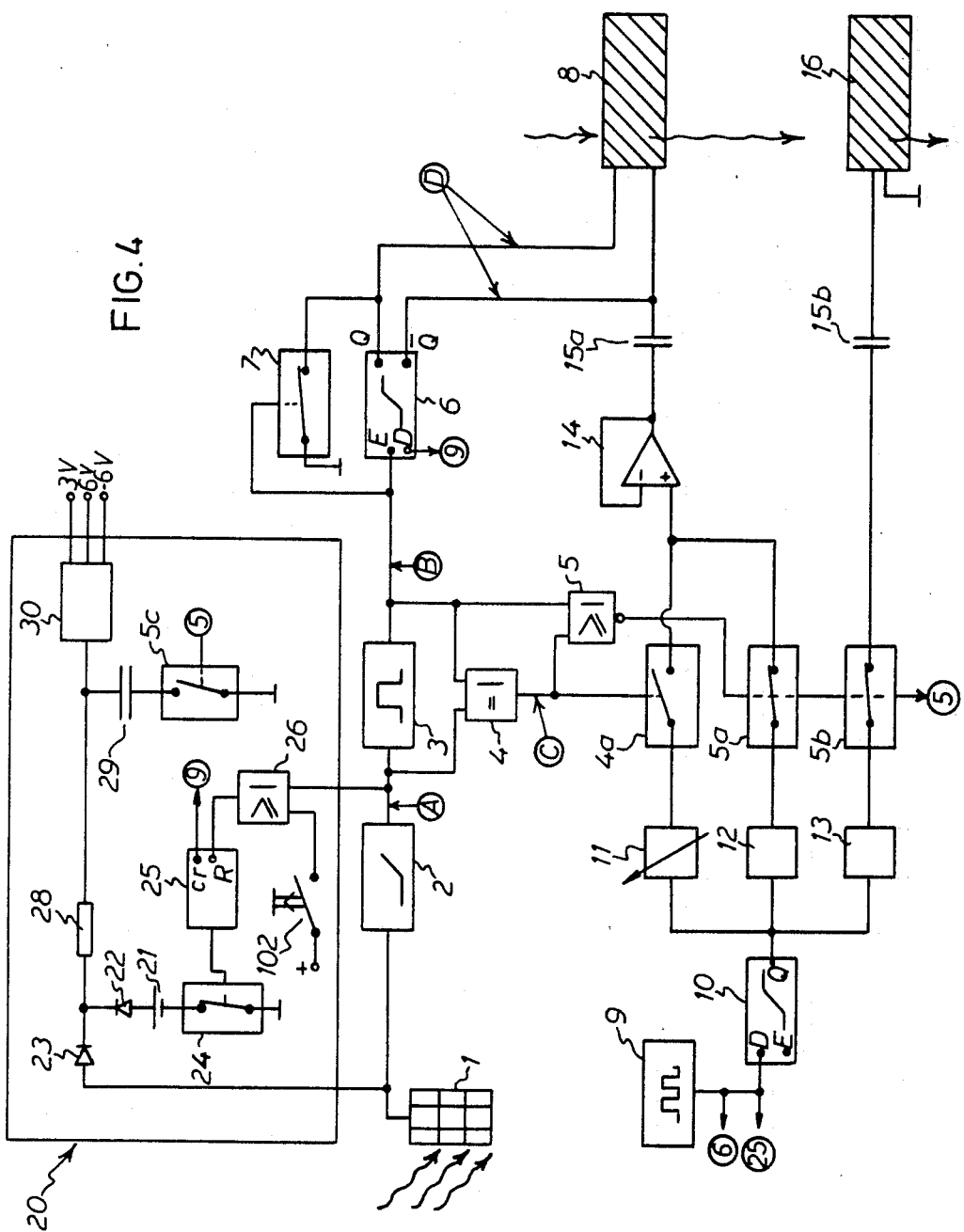
FIG. 4 schematically shows the design of a control circuitry for controlling the optical arrangement of the welder's helmet or visor.

In FIG. 4, there is shown a control circuitry for controlling the transmittance in the optical arrangement 103. The control circuitry has a photocell or solar cell panel 1 which is connected in series with an amplifier or filter unit 2 which substantially acts as a high-pass filter, and with a one-shot 3 which has a time constant of about 50 ms. The output of the one-shot 3 is connected to the enabling input of a first level shifter 6 which, in turn, has two outputs one of which is non-inverted and the other of which is inverted and which are connected to a first and a second input, respectively, of a first positive electro-optical cell 8. The first input of the EO-cell 8 is connectible to earth by means of a switch 7 whose control input is connected to the output of the one-shot 3 and which is closed in the inactivated state, i.e. when the enabling input of the first level shifter 6 is low.

An EXCLUSIVE-OR gate 4 has two inputs connected in parallel over the one-shot 3, and a NOR gate 5 has two inputs connected to the output of the EXCLUSIVE-OR gate 4 and to the output of the one-shot 3. The EXCLUSIVE-OR gate 4 controls a switch 4a which is open in the inactivated state, and the NOR gate 5 controls two switches 5a and 5b both of which are closed in the inactivated state, and one switch 5c which is open in the inactivated state.

An oscillator 9 is connected to the data input of the first level shifter 6 and to the data input of a second level shifter 10 whose non-inverted output, via a variable voltage divider 11 connected in series with the switch 4a or via a voltage divider 12 connected in series with the switch 5a, is connected to a voltage follower 14 whose low-impedance output is connected, via a capacitor 15a, to the second input of the first EO-cell 8.

The non-inverted output of the second level shifter 10 is also connected to a voltage divider 13 which is connected in series with the switch 5b and a capacitor 15b connected to one input of a second negative EO-cell 16 whose other input is grounded.

The control circuitry further comprises a drive circuit which in FIG. 4 is generally designated 20 and which, together with the solar cell panel 1, serves as voltage source for the units included in the control circuitry. The drive circuit 20 has an Li battery 21 whose anode via two series-connected diodes 22 and 23, having their cathode terminals interconnected, is connected to the output of the solar cell panel 1 and whose cathode is connectible to ground via a switch 24. The switch 24 is controlled by an 18-bit binary counter 25 and is open when the counter is reset. The clock pulse input of the counter 25 is connected to the oscillator 9 and the reset input is connected to the output of an OR gate 26 one input of which is connected to the output of the unit 2 and the other input of which is connectible to high potential via the pressure-sensitive switch 102 (cf. FIG. 1) which is arranged for instance on the inside of the welding visor and is closed when putting on the visor. Between the diodes 22 and 23 is connected one end of a resistor 28 whose other end is grounded via a capacitor 29 connected in series with the switch 5c, and also connected to a voltage stabilizing and voltage doubling unit 30. In this embodiment, the unit 30 has three DC outputs of 3 V, 6 V and −6 V for driving the units of the control circuitry.

Each of the level shifters 6 and 10 has an enabling input, a data input, a first output and a second output inverted with respect to the first output. Further, the level shifters have two voltage terminals which are supplied with reference voltages $V_{SS}$ and $V_{DD}$, here 3.2 V and 6 V, respectively, obtained from the drive circuit 20. Both outputs are high-impedance outputs and independent of signals on the data input if the enabling input is low. However, if the enabling input is high, the first output follows the data input in such a manner that a logic "0" on the data input yields $V_{SS}$ on the first output, and a logic "1" on the data input yields $V_{DD}$ on the same output. The voltage on the other output has the same amount, but is of opposite sign, as the voltage on the first output.

The first EO-cell 8 is positive, which means that the transmittance decreases when the voltage across the inputs of the cell increases. The second EO-cell 16 is negative, which means that the transmittance decreases when the voltage applied decreases. This second EO-cell is especially advantageous in respect of safety since any voltage drop-out will result in an immediate attenuation of the welding light in the second EO-cell.

Figure 5:
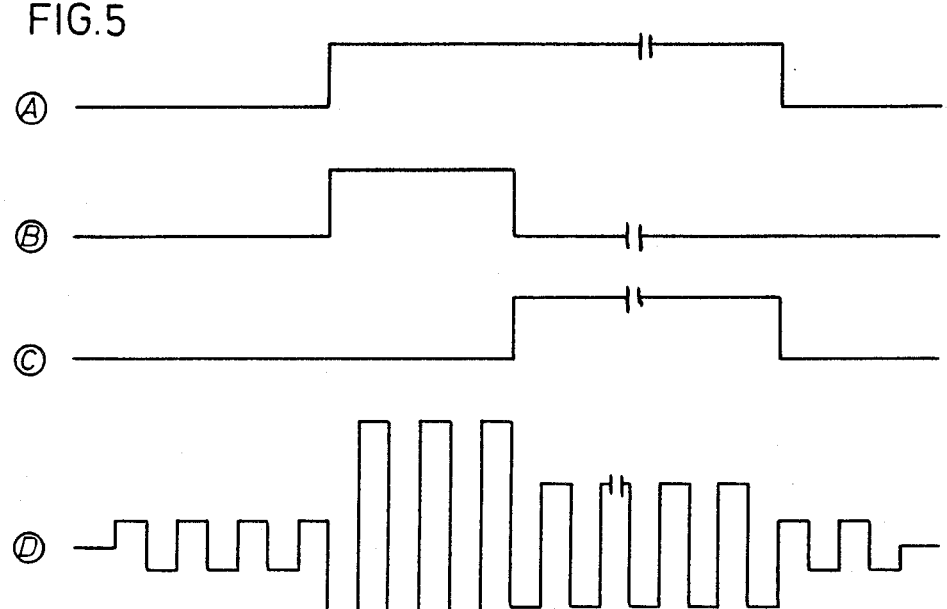
FIG. 5 shows curves corresponding to points A-D in FIG. 4, curve A corresponding to the voltage on the output of the unit 2, curve B corresponding to the voltage on the output of the unit 3, curve C corresponding to the voltage on the output of an EXCLUSIVE-OR gate 4, and curve D corresponding to the voltage between the inputs of a first EO-cell 8.
Figure 6:
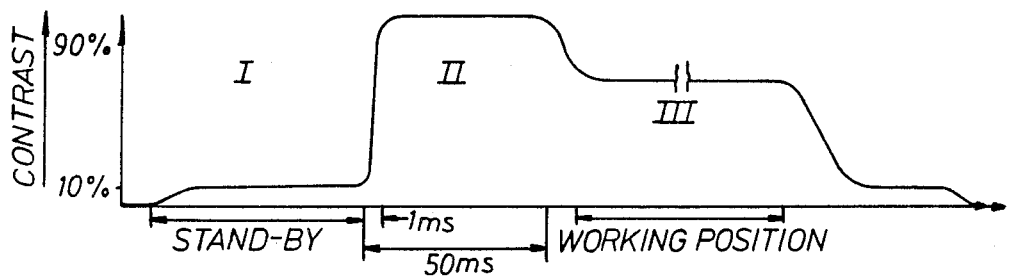
FIG. 6 illustrates how the attenuation in the first EO-cell is controlled between three levels during the welding operation, which is divided into a standby state I, an initiation state II lasting 50 ms, and an operative state III extending to the end of the welding operation.

The mode of operation of the control circuitry will now be described with reference to FIGS. 4–6. FIG. 6 illustrates the contrast (attenuation) in the first EO-cell 8 as a function of time during one welding operation.

Before the welding operation is started, the circuit is in a stand-by state, here called state I, in which the first EO-cell 8 is supplied with a small bias voltage with a view to decreasing the switching time of the cell 8 at the commencement of the welding operation. In FIG. 6 it is shown how the contrast in the cell 8 is substantially increased at the commencement of the welding operation, thereafter to be maintained on a high level for about 50 ms. This initiation state is called state II. After 50 ms, the contrast of the EO-cell 8 decreases slightly but still is substantially higher than the contrast in state I. In this operational state, the control circuitry is in state III.

In the stand-by state I, the solar cell panel 1 has not yet received any welding light and light which may be incident from the ambient atmosphere has such a frequency that the signal produced in the panel 1, because of this light, cannot pass through the amplifier and filter unit 2 whose output thus is constantly low in state I. The one-shot 3 is then not triggered, its output and, hence, also the enabling input of the first level shifter 5 then being low. Both outputs of the first level shifter 6 then have high impedance and, moreover, the non-inverted output is connected to ground via the switch 7 which in this state I is closed. Thus, the first input of the first EO-cell 8 is also grounded.

In state I, the output of the EXCLUSIVE-OR gate 4 is low and the output of the NOR gate 5 is high. This means that the first EO-cell 8 is supplied from the oscillator 9 via the second level shifter 10, the voltage divider 12, the switch 5a, which is closed in state I, the voltage follower 14 and the capacitor 15b which blocks against any DC components in the signal. In this state, the signal path via the switch 4a is blocked.

The voltage division in the voltage divider 12 is so adjusted that the contrast in the EO-cell 8 in stand-by state I becomes relatively low, approximately 10%. In this stand-by state, the second EO-cell 16 is also transparent since it is of the negative type and is now supplied with a voltage signal from the oscillator 9 via the second level shifter 10, the voltage divider 13, the switch 5b, which is closed in this state, and the capacitor 15b. In stand-by state I, the light transmitted through the filter will thus be within the range shown in FIG. 6d.

In stand-by state I, the state in the drive circuit 20 is as follows. Since the pressure-sensitive switch 102 disposed in the visor is closed in this state, the reset input of the counter will be high, which means that the counter 25 is reset and the switch 24 is closed, which, in turn, entails that the Li-battery 21 is connected to the circuit and can drive the different units.

However, if the ambient light is sufficiently strong, it can drive the circuit and the battery is then disconnected by means of the two diodes 22 and 23. During welding, the resistor 28 is connected to the capacitor 29 so as to form a low-pass filter for the strongly frequency-modulated welding light. However, this filter is not engaged in state I in order that the switching of the cells to dark should not be delayed. In the unit 30, the voltage signal received from the solar cell panel 1 or the battery 21 is stabilized and converted into suitable drive and reference voltages.

When the welding operation is started in state II, the following events take place. Frequency-modulated welding light from the welding flame reaches the solar cell panel 1 which produces an AC voltage of such a frequency that the signal can pass through the amplifier and filter unit 2 whose output thus is constantly high. The one-shot 3 is triggered, the output of the one-shot and, hence, the enabling input of the first level shifter 6 being then high for 50 ms. The outputs of the level shifter 6 now follow the input signal on the data input which is connected to the oscillator 9 and between the non-inverted and the inverted output there is now an AC voltage with a peak-to-peak value of 12 V. This AC voltage is now connected directly to the first EO-cell 8 since the switch 7 opens and the ground connection of the first input of the EO-cell 8 is thereby broken.

The EXCLUSIVE-OR gate 4 remains deenergized but the NOR gate is deenergized and the current paths through the switches 5a and 5b are consequently broken when these switches open. During the first 50 ms of the welding time, the first EO-cell 8 is thus supplied only from the first level shifter 6, and the voltage applied to the EO-cell 8 is considerably higher in this state than the voltage which will be supplied to this EO-cell during the rest of the welding time, with a view to decreasing the switching time of the EO-cell 8 to dark.

The voltage supply through the switch 5b to the second negative EO-cell 16 is thus broken at the commencement of the welding operation, and this EO-cell will therefore further attenuate any light which may pass through the first positive EO-cell 8.

At the same time as the output of the unit 2 goes high at the commencement of the welding operation, the OR gate 26 is energized also on its other input. Thus, the counter 25 remains zeroized and the switch 24 closed, such that the battery 21 is engaged in the circuit. If the voltage from the solar cell panel exceeds the battery voltage, this will however be blocked by the diode 22, thus avoiding any unnecessary consumption of the battery voltage. The purpose of the Li-battery primarily is to achieve a sufficiently strong voltage source at the instant of switching to dark before the intensity of the welding light has reached its full value and the voltage from the solar cell panel is sufficient for driving the EO-cells. The switch 5c is now closed and the low-pass filter consisting of the resistor 28 and the capacitor 29 and serving to attenuate the strongly frequency-modulated voltage from the welding light is thus engaged.

When the welding operation has proceeded for 50 ms, the control circuitry passes to the operative state, state III, which is characterised by a voltage across the first EO-cell 8 which is lower than in state II but higher than in state I.

State III is started when the one-shot 3 returns to the untriggered state after 50 ms. The output of the one-shot 3 thus is low, which entails that the first level shifter 6 is deenergized and, consequently, that the first EO-cell 8 cannot be supplied via this level shifter 6, and that the first input of the first EO-cell 8 is grounded via the switch 7, and also that the EXCLUSIVE-OR gate 4 is energized, such that the first EO-cell 8 is now instead supplied from the second level shifter 10 via the variable voltage divider 11, the switch 4a which is now closed, the voltage follower 14 and the capacitor 15a to the second input of the EO-cell 8. Since the first input of this EO-cell 8 is grounded in this state, the resulting voltage across the inputs of the EO-cell in state III will be lower than in state II.

The light transmission through the filter according to the invention in operative state III thus corresponds to the hatched area B in FIG. 3c.

No change takes place in the drive circuit 20 or at the second EO-cell 16 at the transition from state II to the operative state III since the NOR gate remains deenergized and the input signals to It is evident to anyone skilled in the art that a great number of modifications of the embodiments described above are possible within the spirit and scope of the invention such as it is defined in the accompanying claims.

What I claim and desire to secure by Letters Patent is:

1. An optical filter in a protective welding lens assembly having a predetermined field of vision, comprising two parallel electro-optical cells, each of which covers substantially the entire field of vision of the protective welding lens assembly and each of which has a light transmission which is dependent on the voltage applied across two transparent electrodes included in the respective cell and having intermediate layers of liquid crystals, one of said cells being light-transmitting when voltage is applied and light-absorbing when voltage is not applied, the other of said cells being light-transmitting when substantially no voltage is applied and light-absorbing when voltage is applied, wherein at least a first of said cells is nematic with an admixture of dye molecules with anisotropic light absorption, the optical filter further comprising a contrast-enhancing filter sheet which also covers said entire field of vision of the protective welding lens assembly, said filter sheet being disposed in the ray path of the cells and allowing transmission of visible light within a wave-length range in which the first cell is absorbing light in its absorbing condition, and said filter sheet preventing transmission of light within a wavelength range within which the first cell is transmitting light in its absorbing condition, said optical filter having an electric circuit for controlling the transmission of the optical filter by selecting voltages for applying across the electro-optical cells, said electric circuit having a timing circuit for applying a voltage of a short duration which is higher than the subsequent working voltage to said other cell when the optical filter is caused to switch from the transmitting to the absorbing condition, the electric circuit further comprising a high-pass filter and a photodetector whose output serves a voltage supply for said electric circuit and, via said high-pass filter, is connected to the trigger input of the timing circuit for triggering the timing circuit when the photodetector receives light modulated by frequencies above the limit frequency of the high-pass filter.

2. An optical filter as claimed in claim 1, wherein the filter sheet is arranged on the light-exit side of the first cell.

3. An optical filter as claimed in claim 1, wherein the first cell is arranged on the light-exit side of the second cell for receiving plane-polarized light therefrom.

4. An optical filter as claimed in claim 1, wherein the other cell is nematic without admixture of dye molecules with anisotropic light absorption and on either side of the transparent electrodes has a polarizing filter.

5. An optical filter as claimed in claim 1, wherein both electro-optical cells are nematic with admixture of dye molecules with anisotropic light absorption.

6. An optical filter as claimed in claim 1, further comprising battery means serving as a voltage supply for said electric circuit, and means responsive to the output of said photodetector for disconnecting said battery means from said electric circuit.

* * * * *